(12) United States Patent
Deflorian et al.

(10) Patent No.: US 11,951,236 B2
(45) Date of Patent: Apr. 9, 2024

(54) AIR FRESHENER FOR VEHICLES

(71) Applicant: ZOBELE HOLDING S.P.A., Trento (IT)

(72) Inventors: Stefano Deflorian, Trento (IT); Walter Sordo, Trento (IT)

(73) Assignee: ZOBELE HOLDING S.P.A. (IT)

( * ) Notice: Subject to any disclaimer, the term of this patent is extended or adjusted under 35 U.S.C. 154(b) by 363 days.

(21) Appl. No.: 17/069,619

(22) Filed: Oct. 13, 2020

(65) Prior Publication Data

US 2021/0023253 A1    Jan. 28, 2021

Related U.S. Application Data

(63) Continuation of application No. 15/780,333, filed as application No. PCT/EP2016/079101 on Nov. 29, 2016, now Pat. No. 10,835,630.

(30) Foreign Application Priority Data

Dec. 4, 2015  (EP) ..................................... 15198023

(51) Int. Cl.
*A61L 9/12* (2006.01)
*B60H 3/00* (2006.01)

(52) U.S. Cl.
CPC .............. *A61L 9/12* (2013.01); *B60H 3/0007* (2013.01); *A61L 2209/15* (2013.01)

(58) Field of Classification Search
CPC ...... A61L 9/12; A61L 2209/15; B60H 3/0007
See application file for complete search history.

(56) References Cited

U.S. PATENT DOCUMENTS

| | | | |
|---|---|---|---|
| 5,407,642 A | 4/1995 | Lord | 422/122 |
| 7,687,038 B2 | 3/2010 | Wheatley | 422/124 |
| 2005/0127538 A1 | 6/2005 | Fabrega et al. | 261/104 |
| 2010/0314461 A1* | 12/2010 | Gruenbacher | B60H 3/0028 239/6 |
| 2013/0266486 A1 | 10/2013 | Wu | 422/123 |
| 2014/0161672 A1 | 6/2014 | Wheatley et al. | 422/123 |

FOREIGN PATENT DOCUMENTS

EP    1 486 365 A2    12/2004

OTHER PUBLICATIONS

International Search Report dated Feb. 24, 2017 in corresponding PCT International Application No. PCT/EP2016/079101.
Written Opinion dated Feb. 24, 2017 in corresponding PCT International Application No. PCT/EP2016/079101.

* cited by examiner

*Primary Examiner* — Sean E Conley
*Assistant Examiner* — Brendan A Hensel
(74) *Attorney, Agent, or Firm* — OSTROLENK FABER LLP

(57) ABSTRACT

An air freshener for vehicles includes a main body for holding a container for volatile substances and a foldable clip that may be placed in a substantially perpendicular position with respect to the main body. The foldable clip is rotatable with respect to the main body. The clip may always be connected with the main body, so that it is sold with it occupying a reduced space in the package. The clip may be rotated to be adapted to any kind of ventilation grids.

5 Claims, 4 Drawing Sheets

AIR FRESHENER FOR VEHICLES

CROSS-REFERENCE TO RELATED APPLICATIONS

The present patent application is a continuation application of prior U.S. patent application Ser. No. 15/780,333, filed May 31, 2018, by Stefano DEFLORIAN and Walter SORDO, entitled "AIR FRESHENER FOR VEHICLES," which is a 35 U.S.C. §§ 371 national phase application of PCT/EP2016/079101, filed Nov. 29, 2016, which claims priority to European Patent Application No. 15198023.2, filed Dec. 4, 2015, the entire contents of which applications are incorporated herein by reference. The PCT International Application was published in the English language.

FIELD OF THE DISCLOSURE

The present disclosure is air fresheners for vehicles, in particular, an air freshener that includes a clip for attachment to a ventilation grid of the vehicle.

BACKGROUND OF THE INVENTION

Air fresheners for vehicles to be mounted on the ventilation grid of the dashboard are well known and they are having a big commercial success.

The air fresheners for vehicles always comprise a clip for their attached to the ventilation grid of the vehicle and this clip extends in a perpendicular direction from the main body of the air freshener.

Generally, the main body and the clip of the air freshener are sold separately, i.e. not assembled, and the user assembles them before its first use. This for several reasons:
- Keep the packaging as flat as possible and then reduce overall size of the goods during transportation and on the shelf.
- Allow to the user to assemble the clip with a different orientation (vertical/horizontal) depending of the orientation of the grid of the vehicle.

The fact the clip is sold separated from the main body can have several drawbacks:

The user can lose the clip, or the user could not notice of its presence in the packaging, so that the clip is discarded with the packaging, resulting in the impossibility to use of the air freshener on the ventilation grid of the vehicle.

Furthermore, the user can assemble the clip incorrectly.

It is known an air freshener with a preassembled clip that is folded before its first use, and the user has rotated it to place it in the perpendicular direction. However, the main aim of this solution is not to solve the issue above, but to activate the refill, even though this solution solves the issue above. Nevertheless, this kind of air fresheners does not allow to the user to select the orientation of the clip.

Therefore, there is still the need of an air freshener for vehicles, in which the foldable clip allows the positioning of the device on both vertical and horizontal ventilation grids of the vehicles.

DESCRIPTION OF THE INVENTION

With the air freshener of the invention said drawbacks can be solved, presenting other advantages that will be described hereinafter.

The air freshener for vehicles according to the present invention comprises a main body for holding a container for volatile substances and a foldable clip which can be placed in a substantially perpendicular position with respect to the main body, and it is characterized in that said foldable is rotatable with respect to the main body.

Thanks to these features, the clip is always connected with the main body, so that it is sold with it occupying a reduced space in the package. Furthermore, the clip can be rotated to be adapted to any kind of ventilation grids.

Preferably, said main body comprises a base including a pin complementary with a groove in the clip, so that when the clip is placed in said substantially perpendicular position, said pin is housed inside said groove. This pin prevents the clip to be detached from this position.

Furthermore, said clip can also comprise a protrusion complementary with a hole in the base, so that when the clip is placed in said substantially perpendicular position, said protrusion is housed inside said hole. This protrusion provides a more precise guiding and a higher mechanical resistance of the clip/base once assembled.

Advantageously, said clip comprises a rim, and said groove can be placed in said rim, and said rim preferably comprises a rod defining a hinge, said rod being circumscribed to a circle defined by the rim.

Furthermore, said base preferably comprises a plurality of retainers, which engage with the rim of the clip when the clip is placed in said substantially perpendicular position.

BRIEF DESCRIPTION OF THE DRAWINGS

For a better comprehension of what has been disclosed, some drawings are attached in which, diagrammatically and only as a non-limitative example, a practical embodiment is shown.

DESCRIPTION OF A PREFERRED EMBODIMENT

Figure 1:
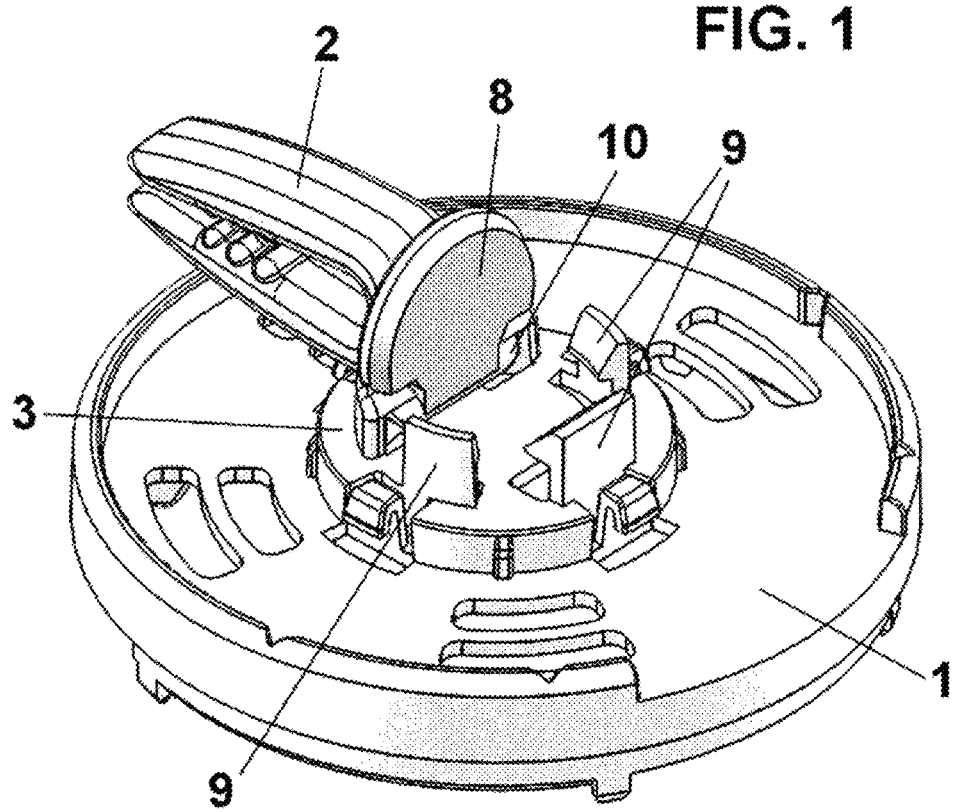
FIG. 1 is a perspective view of the air freshener of the present invention, according to a first embodiment.

The air freshener for vehicles according to the present invention comprises a main body 1, usually substantially flat, an according to the shown embodiment with a disk shape.

This main body 1 holds a container for volatile substances, which is not shown in the drawings.

The air freshener also comprises a clip 2 for fixing the air freshener to a ventilation grid of a vehicle. This clip 2 is foldable and is mounted to the main body 1 by a rod 10 defining a hinge, this hinge being also defined by a housing for said rod 10. The clip 2 can be placed in a use position, in which the clip 2 is substantially perpendicular with respect to the main body 1, as shown in FIG. 3, and the clip 2 is preferably placed in a base 3 of the main body 1.

Figure 5:
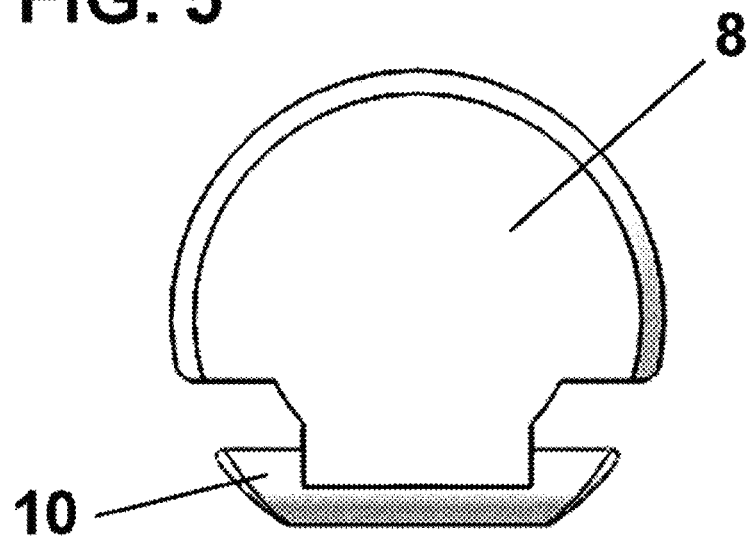
FIG. 5 is a rear view of the clip of the air freshener for vehicles according to the present invention, showing the rim and rod defining the hinge.

Furthermore, the clip 2 comprises a rim 8, which in the use position is in contact with the base 3 and retained by a plurality of retainers 9 of the base 3. Said rod 10 defining the hinge is preferably placed in the rim 8 and said rod 10 being placed inside a circle defined by the rim 8, as shown in FIG. 5.

Therefore, the air freshener according to the invention is sold with the clip 2 attached to the main body 1 and the clip 2 can be rotated to be adapted to the (horizontal or vertical) grid of the vehicle.

Figure 2:
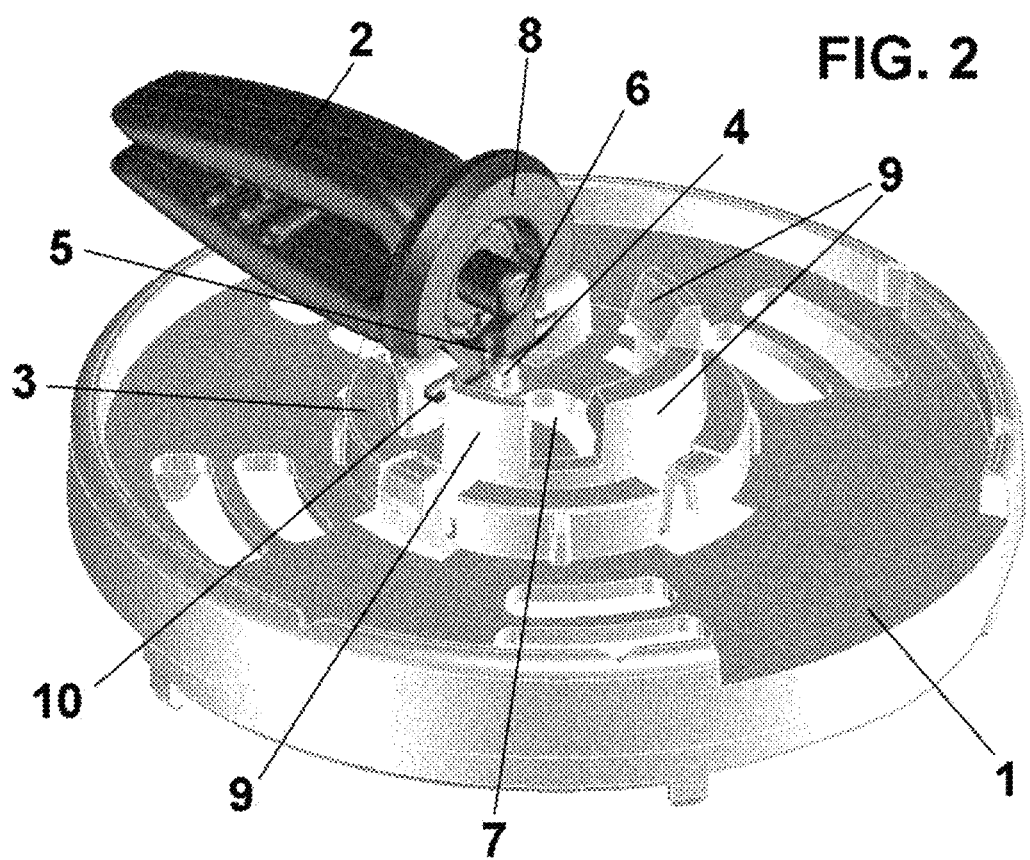
FIG. 2 is a perspective view of the air freshener of the present invention, according to a second embodiment.
Figure 3:
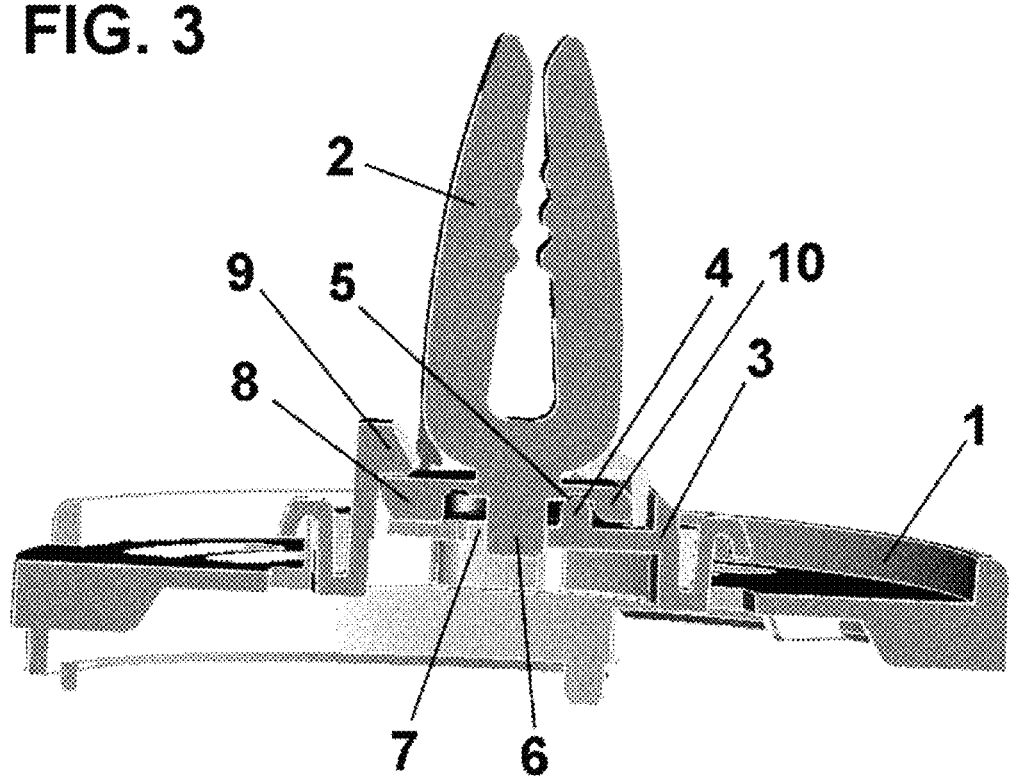
FIG. 3 is a cross-sectional view of the second embodiment of the air freshener according to the invention in its use position.
Figure 4:
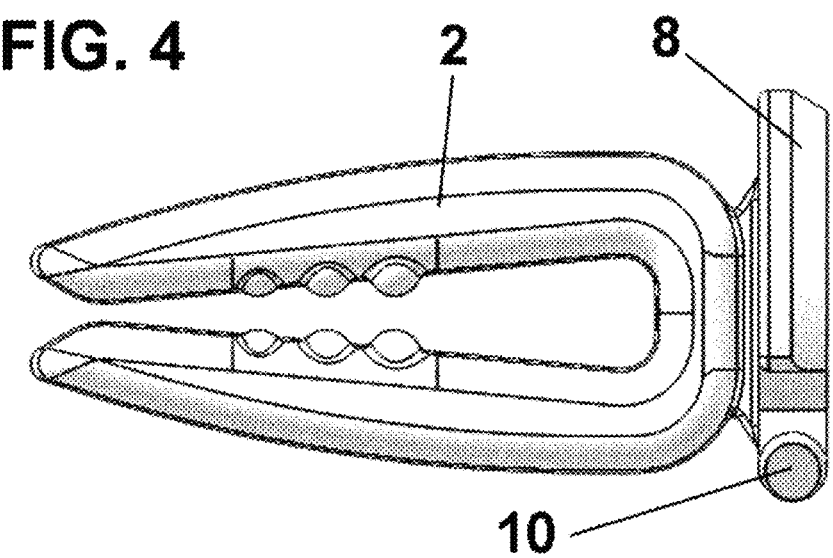
FIG. 4 is a lateral view of the clip of the air freshener for vehicles according to the present invention.

In FIGS. 2 and 3 a second embodiment of the air freshener according to the invention is shown. For simplicity reasons, the same elements than in the first embodiment are designed by the same numeral references, and these elements will not be described again.

According to this second embodiment, the base 3 comprises a pin 4, which is complementary with a groove 5 of the clip 2, said groove 5 being placed in the rim 8 of said clip 2. This pin 4 prevents the clip 2 to be detached o rotated from its use position.

In this case, the clip 2 can also comprise a protrusion 6 at the center defined by the rim 8, which in the use position of the clip 2 is housed inside a complementary hole 7. This protrusion 6 provides a more precise guiding and a higher mechanical resistance of the clip 2.

The use of the air freshener according to the invention is easier than the prior art air fresheners. The user just rotates the clip 2 to its use position, and he/she rotates the clip 2 to the desired orientation, according to the ventilation grid of the vehicle.

Even though reference is made to a specific embodiment of the invention, it is clear for a person skilled in the art that the disclosed air freshener is susceptible of variations and modifications, and that all the details cited can be substituted by other technically equivalent ones, without departing from the scope of protection defined by the attached claims.

The invention claimed is:

1. An air freshener for vehicles, the air freshener comprising:
    a main body comprising a base and configured to hold a container for volatile substances; and
    a foldable clip comprising a rim and configured to be placed in a substantially perpendicular position with respect to the main body,
    wherein said foldable clip is rotatable with respect to the base of the main body,
    wherein said foldable clip is mounted to the main body by a hinge, the hinge being defined by a rod and a housing for said rod, and
    wherein the rod is placed inside a circle defined by the rim,
    wherein the main body comprises:
    a pin complementary with a groove in the clip,
    wherein when the clip is placed in said substantially perpendicular position, said pin is housed inside said groove, and
    wherein said base comprises a plurality of retainers that engage with the rim of the clip when the clip is placed in said substantially perpendicular position.

2. The air freshener for vehicles according to claim 1, wherein said clip comprises a protrusion complementary with a hole in the base,
    wherein when the clip is placed in said substantially perpendicular position, said protrusion is housed inside said hole.

3. The air freshener for vehicles according to claim 1, wherein said groove is placed in said rim.

4. The air freshener for vehicles according to claim 1, wherein said rim comprises the rod of the hinge, the rod forming the hinge with the base.

5. The air freshener for vehicles according to claim 4, wherein said rod is placed inside a circle defined by the rim.

\* \* \* \* \*